(12) United States Patent  (10) Patent No.: US 6,696,021 B1
Bertling  (45) Date of Patent: Feb. 24, 2004

(54) DEVICE FOR ANALYZING BIOLOGICAL AND MEDICAL SPECIMENS

(76) Inventor: Wolf Bertling, Meisenweg 22-91056, Erlangen (DE)

( * ) Notice: Subject to any disclaimer, the term of this patent is extended or adjusted under 35 U.S.C. 154(b) by 0 days.

(21) Appl. No.: 09/142,736
(22) PCT Filed: Mar. 13, 1997
(86) PCT No.: PCT/DE97/00513
§ 371 (c)(1),
(2), (4) Date: Jan. 25, 1999
(87) PCT Pub. No.: WO97/34699
PCT Pub. Date: Sep. 25, 1997

(30) Foreign Application Priority Data

Mar. 15, 1996 (DE) .......................... 196 10 146

(51) Int. Cl.$^7$ .............................................. G01N 21/01
(52) U.S. Cl. ........................ 422/68.1; 422/55; 422/58; 422/99; 422/102; 422/104; 435/287.2; 435/288.7
(58) Field of Search .................... 422/55, 58, 68.1, 422/99, 102, 104; 435/287.2, 287.6, 288.4, 288.7; 204/451

(56) References Cited

U.S. PATENT DOCUMENTS

| 3,915,647 A | * | 10/1975 | Wright .................... 23/253 TP |
| 4,714,590 A | * | 12/1987 | Guigan ........................ 422/102 |
| 4,725,406 A | * | 2/1988 | Compton et al. .............. 422/58 |
| 5,188,963 A | * | 2/1993 | Stapleton .................... 435/299 |
| 5,281,516 A | * | 1/1994 | Stapleton et al. .............. 435/3 |
| 5,346,672 A | * | 9/1994 | Stapleton et al. ........... 422/102 |
| 5,436,129 A | * | 7/1995 | Stapleton ........................ 435/6 |
| 5,451,500 A | * | 9/1995 | Stapleton ........................ 435/6 |
| 5,567,617 A | * | 10/1996 | Caprio et al. ............. 435/287.2 |
| 5,856,211 A | * | 1/1999 | Tonazzi et al. ................ 438/69 |
| 5,955,029 A | * | 9/1999 | Wilding et al. ............. 422/68.1 |
| 5,985,555 A | * | 11/1999 | Bertling ......................... 435/6 |
| 5,993,740 A | * | 11/1999 | Niyamma et al. ............. 422/52 |
| 6,203,304 B1 | * | 3/2001 | Lopez Tonazzi et al. ... 425/110 |

FOREIGN PATENT DOCUMENTS

| DE | 218 959 A1 | 2/1985 | |
| DE | 35 29 792 A1 | 2/1986 | |
| DE | 3500385 A | * 9/1986 | ............ A61M/1/36 |
| DE | 37 36 027 A1 | 3/1989 | |
| DE | G 91 12 403.4 | 2/1992 | |
| DE | G 92 03 917.0 | 6/1992 | |
| DE | 43 05 405 C 1 | 5/1994 | |
| DE | 44 09 436 A 1 | 9/1995 | |
| EP | 0 662 345 A1 | 5/1995 | |
| EP | 674009 A2 | * 9/1995 | |
| EP | 0 687 502 A3 | 10/1996 | |
| FR | 2 718 253 | 3/1994 | |

OTHER PUBLICATIONS

Merriam–Webster Inc. Collegiate Dictionary, tenth edition, pp. 168.*

* cited by examiner

Primary Examiner—Maureen M. Wallenhorst
(74) Attorney, Agent, or Firm—VanOphem & VanOphem, P.C.

(57) ABSTRACT

The invention relates to a device for analyzing biological or medical specimens, such as nucleic acids, tissue and the like, in which a closure element is provided for the leaktight closure of a preparation chamber formed in a basic body, the preparation chamber being connected to at least one first duct, through which substance can be introduced into and removed from the preparation chamber when the closure element is closed.

11 Claims, 9 Drawing Sheets

DEVICE FOR ANALYZING BIOLOGICAL AND MEDICAL SPECIMENS

BACKGROUND OF THE INVENTION

A disadvantage of a device for analyzing biological or medical specimens is that human material, such as tissue, hairs or other epithelial cells, may undesirably infiltrate from the air into the specimen to be analyzed. Precisely in the case of the analysis of human nucleic acids, however, it is necessary to pay particular attention to ensuring that such contamination is avoided.

The object of the present invention is to avoid this disadvantage of the prior art.

BRIEF SUMMARY OF THE INVENTION

According to the invention, a closure element is provided for the leaktight closure of a preparation chamber formed in a basic body. The preparation chamber is connected to at least one first duct, through which substance can be introduced into and removed from the preparation chamber when the closure element is closed. Contamination of the specimen material can thereby be avoided. It is possible, at the same time, to treat the specimen material, for example, with reagents or substances necessary for analysis.

The closure element is expediently a lid which is designed to be transparent, at least in portions, and which is pivotably connected to the basic body. The basic body itself may be produced, at least in portions, from translucent material. It is thus possible to use the device according to the invention for both reflected light and transmitted light methods of microscopic analysis.

In order to rule out contamination of the specimen completely, the first duct may preferably be designed to be closable. For this purpose, the duct may also be provided, for example, with a connection produced in the form of an automatically closing coupling.

The bottom of the basic body is appropriately produced from a material, the thermal conductivity of which is higher than that of the material of the lid. In this case, the bottom is preferably produced from metal, such as aluminum, or a precious metal, such as gold. In order to set the reaction temperature suitable for analysis, the bottom may have a heating and/or cooling device. For special uses, it is also conceivable to provide the bottom with special coatings, such as silanization.

The height of the preparation chamber is preferably 0.01–10 mm. The length of the preparation chamber is in the range of between 5 and 150 mm, and the width is in the range of between 1 and 50 m. The volume may be 1 ml—1 ml.

In a particularly universal version of the device according to the invention, electrodes or capacitor plates are provided on the basic body. These may be arranged in such a way that they are directly in contact with the preparation chamber. The electrodes or capacitor plates are expediently provided in a mutually opposite arrangement in the basic body. They are preferably produced from precious metals, such as platinum, gold or the like.

According to a further design feature, a gel block may be provided in the preparation chamber, the gel block having a preparation area separated by a permeable barrier. This embodiment of the invention serves for conducting electrophoretic analyses. In this case, at least one second duct may be provided, through which substance can be introduced into and removed from the preparation area when the closure element is closed.

In order, in particular, to avoid air inclusions below the lid which impair the observation of the specimen material and to always ensure that the lid is arranged parallel to the bottom, the lid may have, on the inside facing the preparation chamber, a projection with spacers, via which the lid, when in the closed state, can be supported against the bottom of the basic body.

Further objects, features and advantages of the invention will become apparent from a reading of the detailed description thereof take in conjunction with the accompanying drawings.

DETAILED DESCRIPTION OF THE INVENTION

Figure 1:
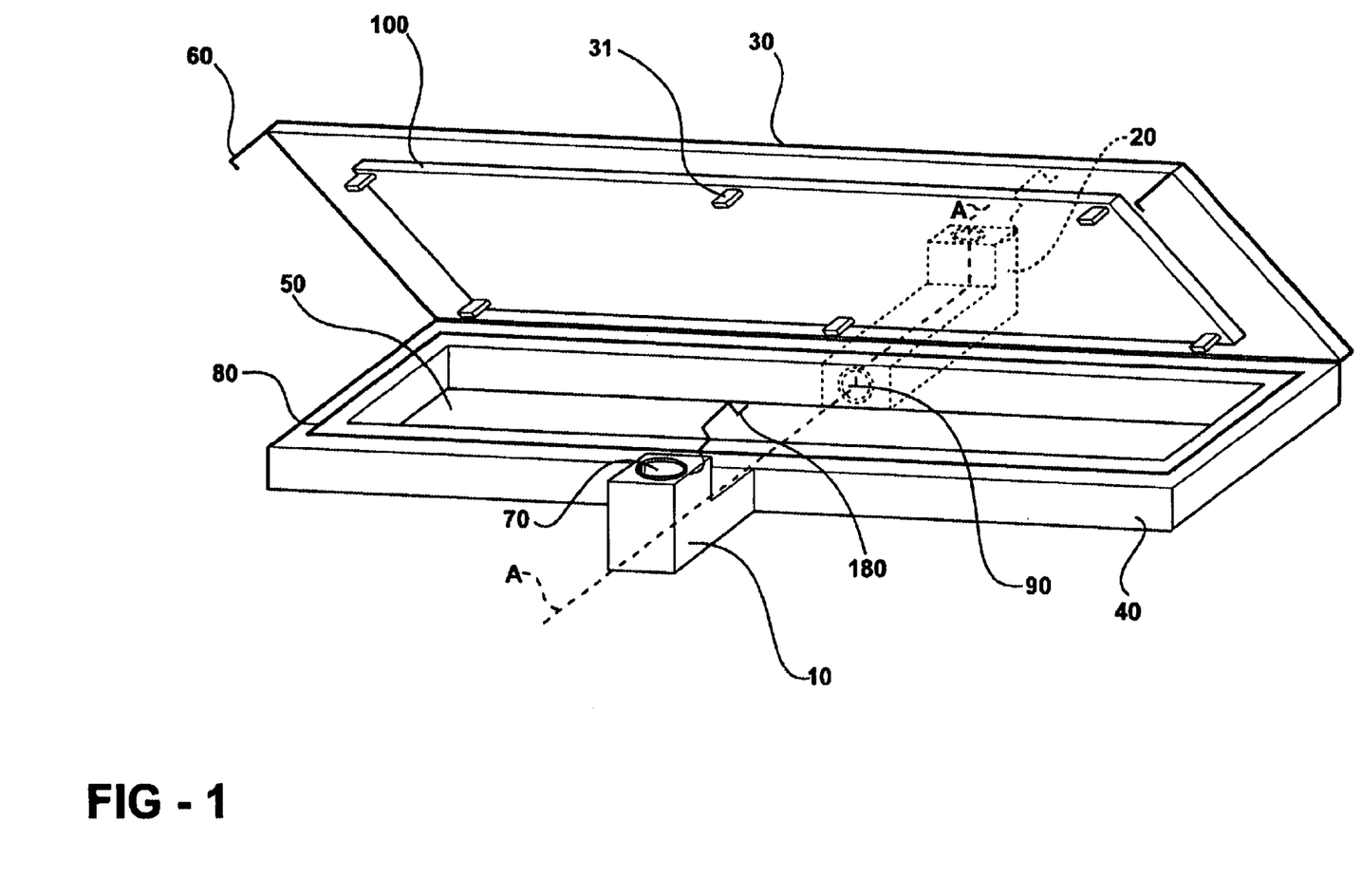
FIG. 1 is a perspective view of a first exemplary embodiment of the invention.

FIG. 1 shows a first exemplary embodiment of the invention. A boxlike basic body 40 manufactured from translucent plastic has, inside it, a preparation chamber 50 which can be closed by means of a lid on the inside facing the preparation chamber 50, a projection 100 which is provided along the edge with spacers 31. Hooklike locking elements 60 are injection molded on two corners of the lid 30. A first peripheral seal 80 is provided on the contact face between the lid 30 and the basic body 40.

The device has, furthermore, a first connection piece 10 and a second connection piece 20, outer orifices 70 of which can in each case be closed by means of a snap lid 180. The first connection piece 10 and the second connection piece 20 open in each case into the preparation chamber 50 in an inner orifice 90.

Figure 2:
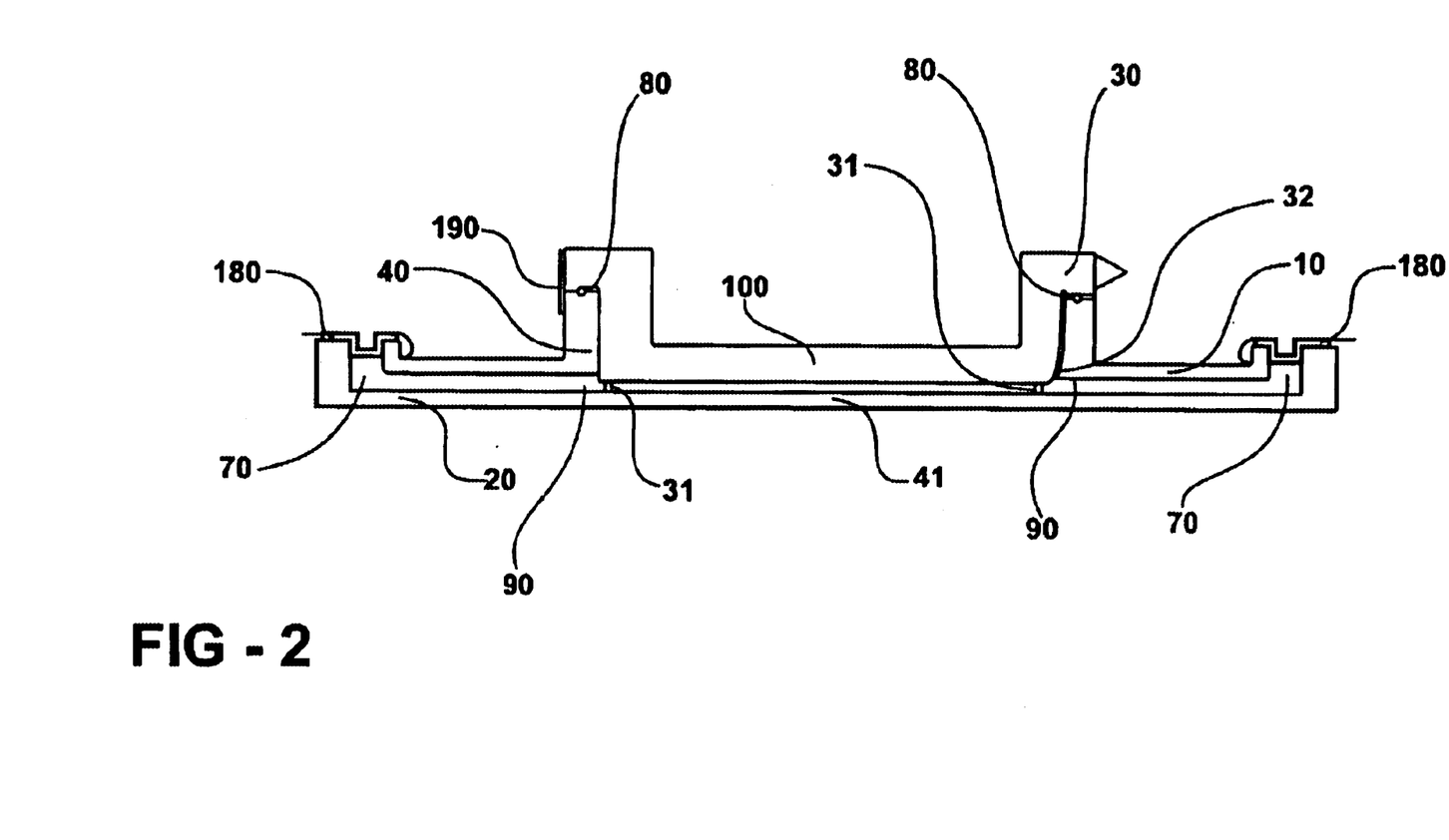
FIG. 2 is a cross section taken along the sectional line A–A' in FIG. 1, illustrating the lid of the device in closed configuration.
Figure 3:
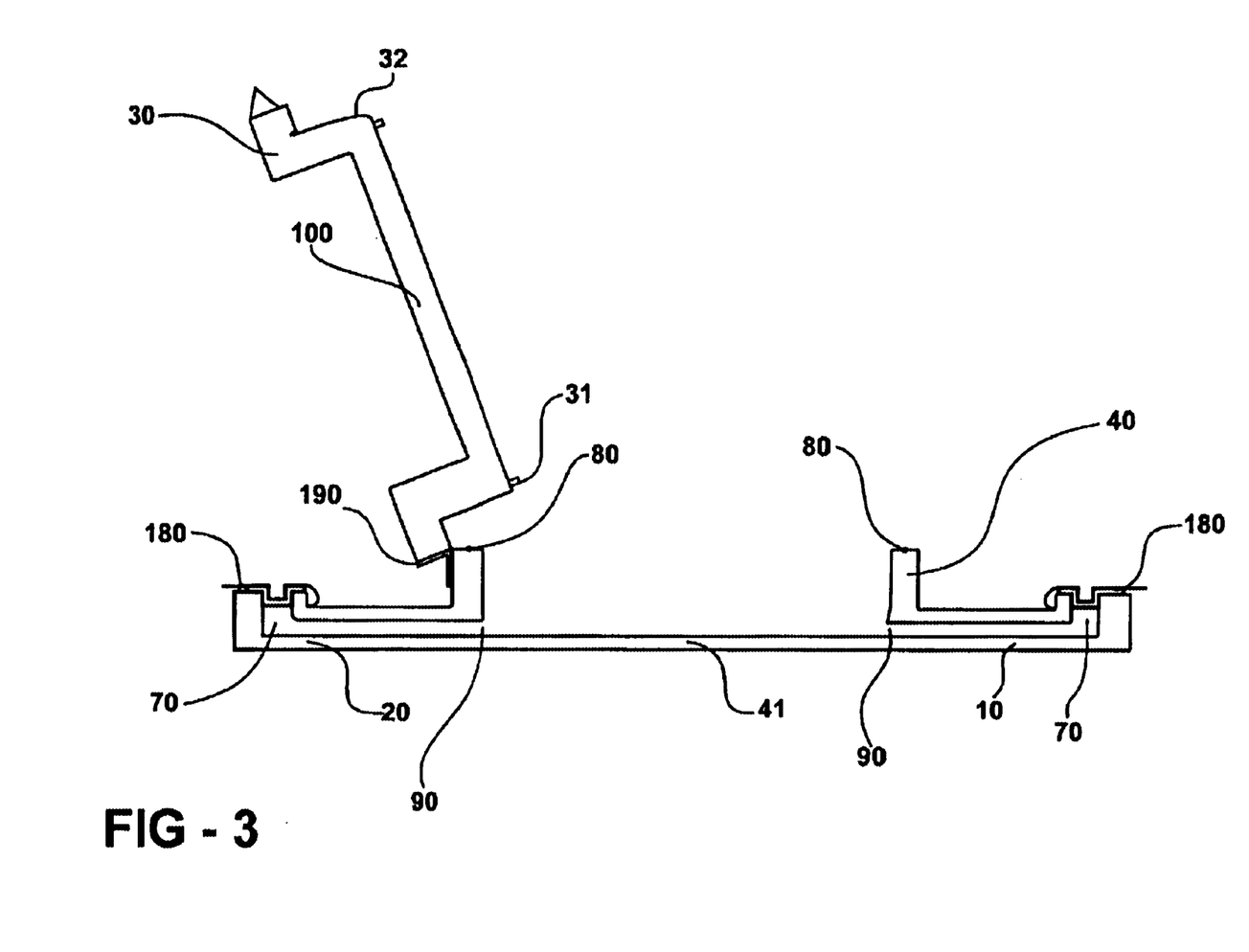
FIG. 3 is a cross section according to FIG. 2, with the lid being open.

As is evident from FIGS. 2 and 3, the lid 30 is held pivotably on the basic body 40 by means of a hinge 190 which may preferably be designed as a film hinge. The projection 100 is supported against a bottom 41 of the basic body 40 via the spacers 31. The lid has a radius 32 on the side located opposite the hinge 190.

Figure 4:
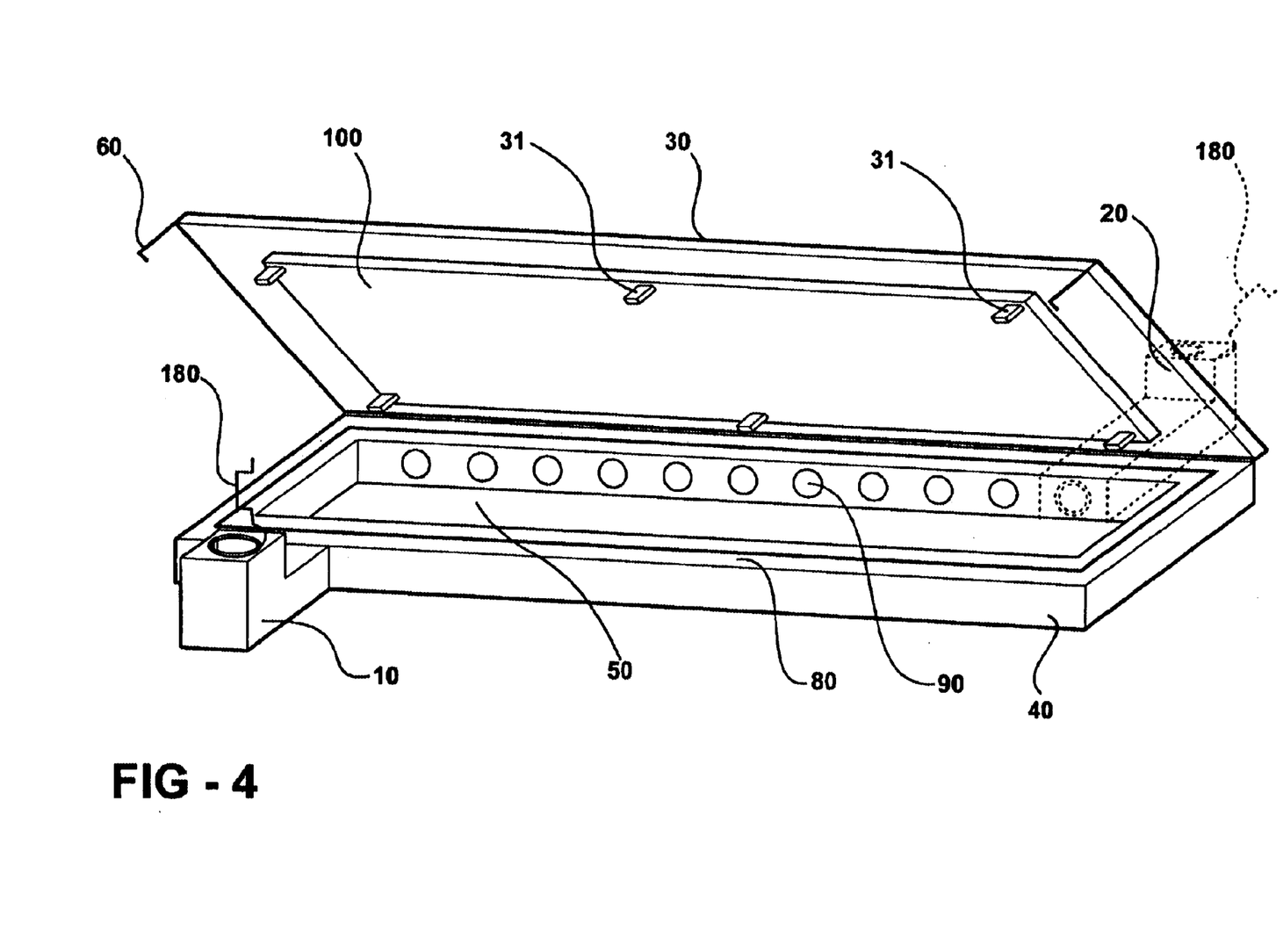
FIG. 4 is a perspective view of a second embodiment of the invention.

In the second exemplary embodiment of the invention shown in FIG. 4, the second connection piece 20 is connected to the preparation chamber 50 via a plurality of inner orifices 90.

Figure 5:
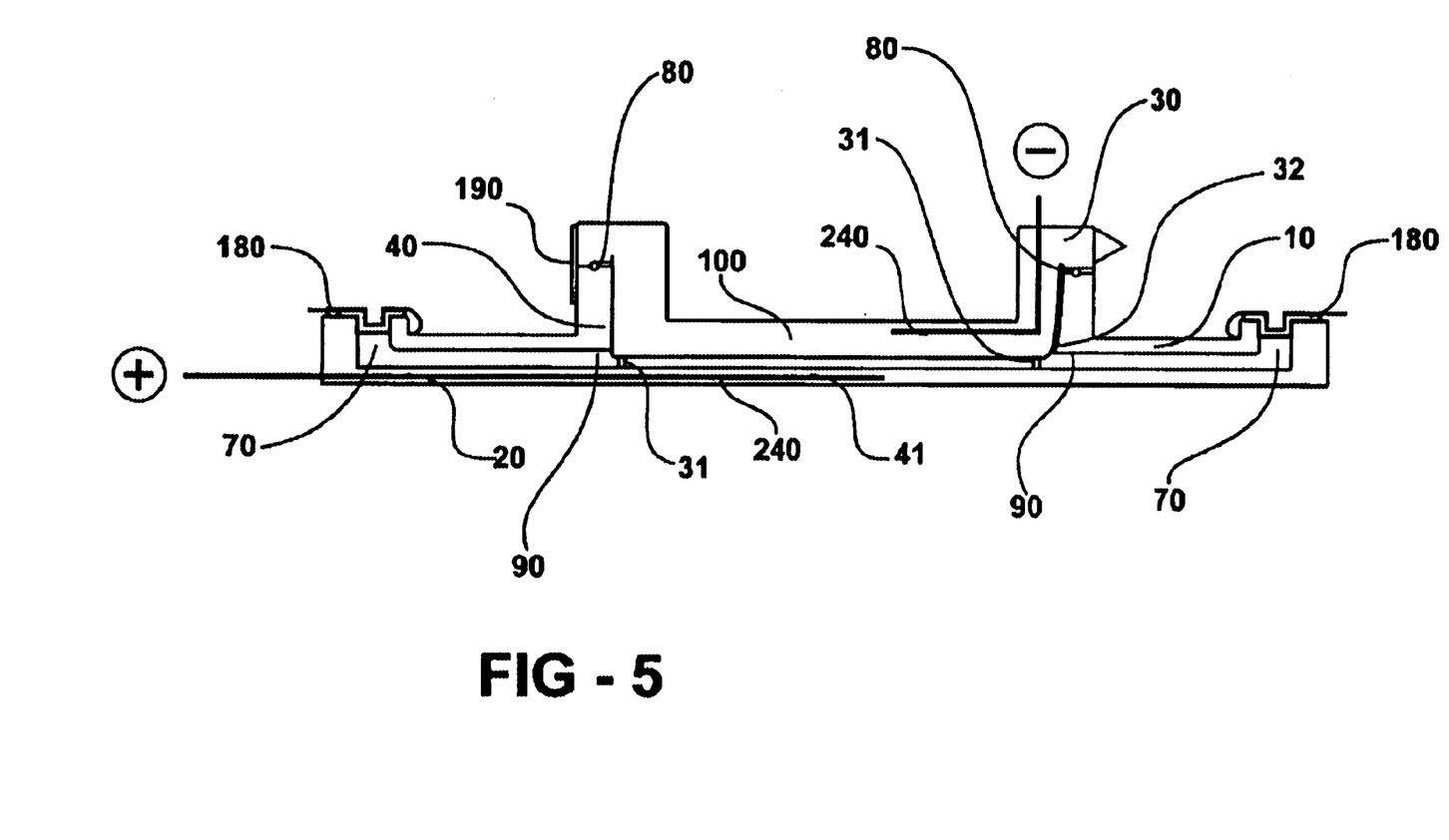
FIG. 5 is a cross section of a third embodiment of the invention.

As illustrated in FIG. 5, according to a third exemplary embodiment of the invention the lid 30 and the bottom 41 may be provided with electrodes 240.

Figure 6:
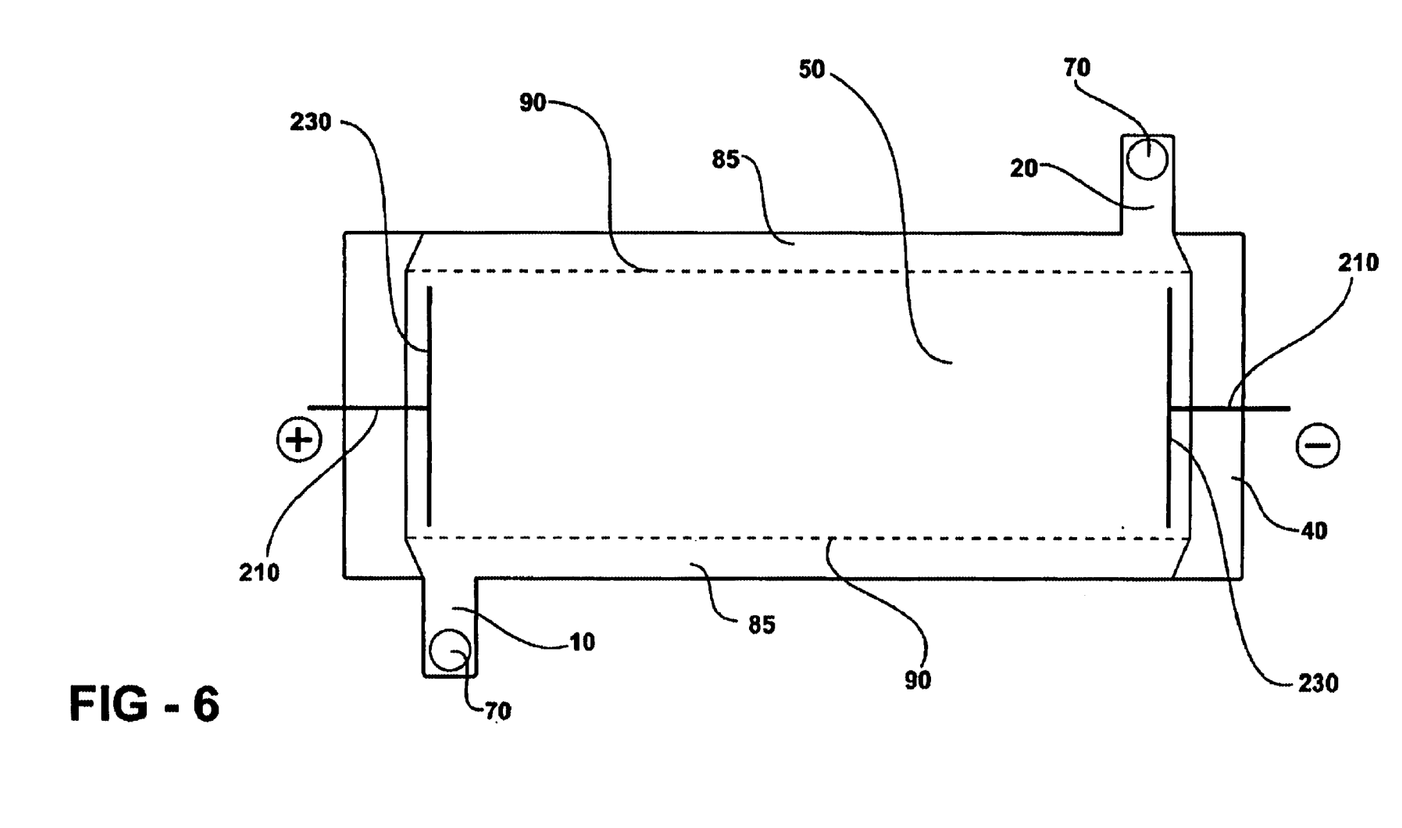
FIG. 6 is a plan view of a fourth embodiment of the invention.

In the fourth exemplary embodiment of the invention illustrated in FIG. 6, capacitor plates 230 provided with terminals 210 are arranged in the region of the opposite short inner walls of the preparation chamber 50. The first connection piece 10 and the second connection piece 20 in each case are connected to a reagent conduit 85 which runs in the region of the long side walls of the basic body 40 and which is provided in each case with a plurality of inner orifices 90.

Figure 7:
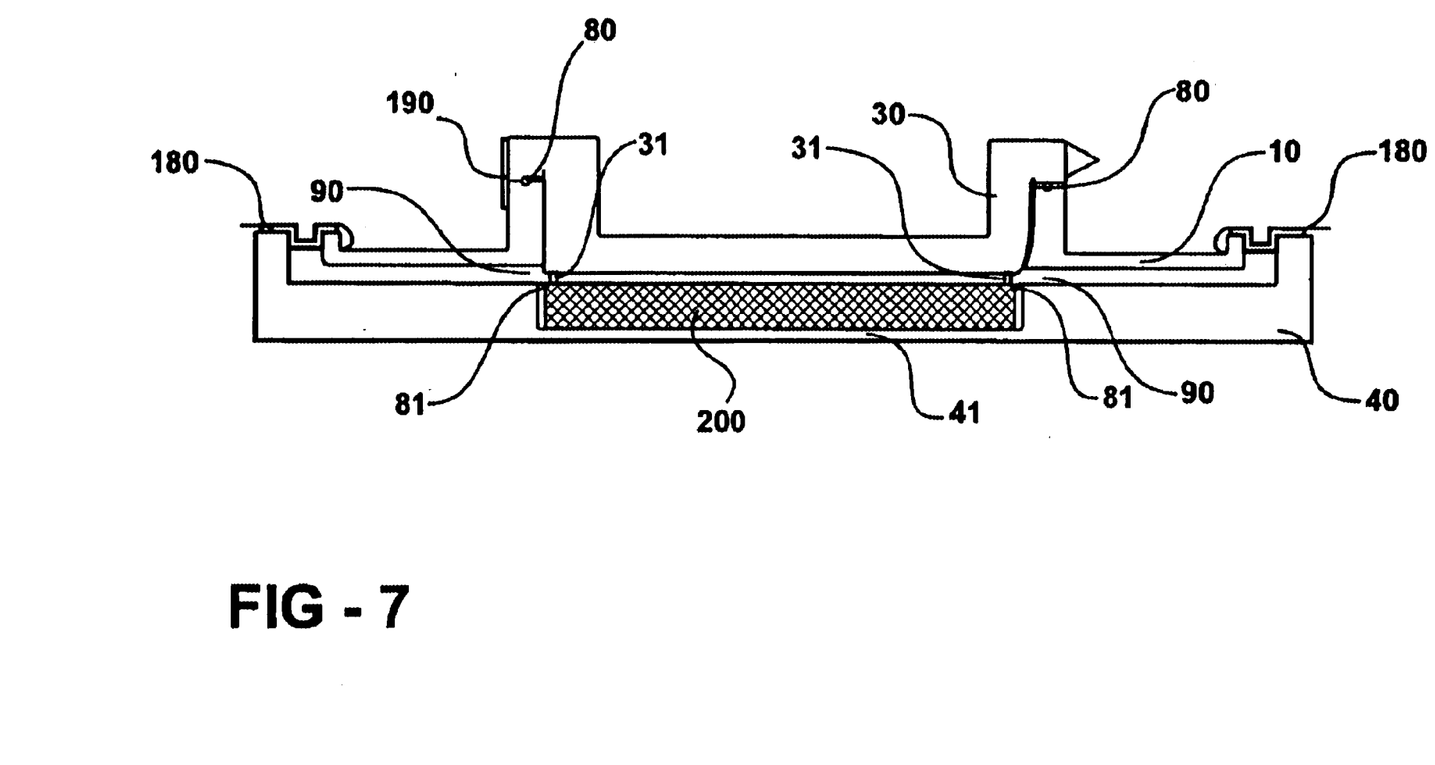
FIG. 7 is a cross section of a fifth embodiment of the invention.

The fifth exemplary embodiment of the invention shown in FIG. 7 has, on the bottom 41, a depression for receiving a specimen carrier 200. A peripheral second seal 81 seals off the specimen carrier relative to the depression provided in the bottom 41.

Figure 8:
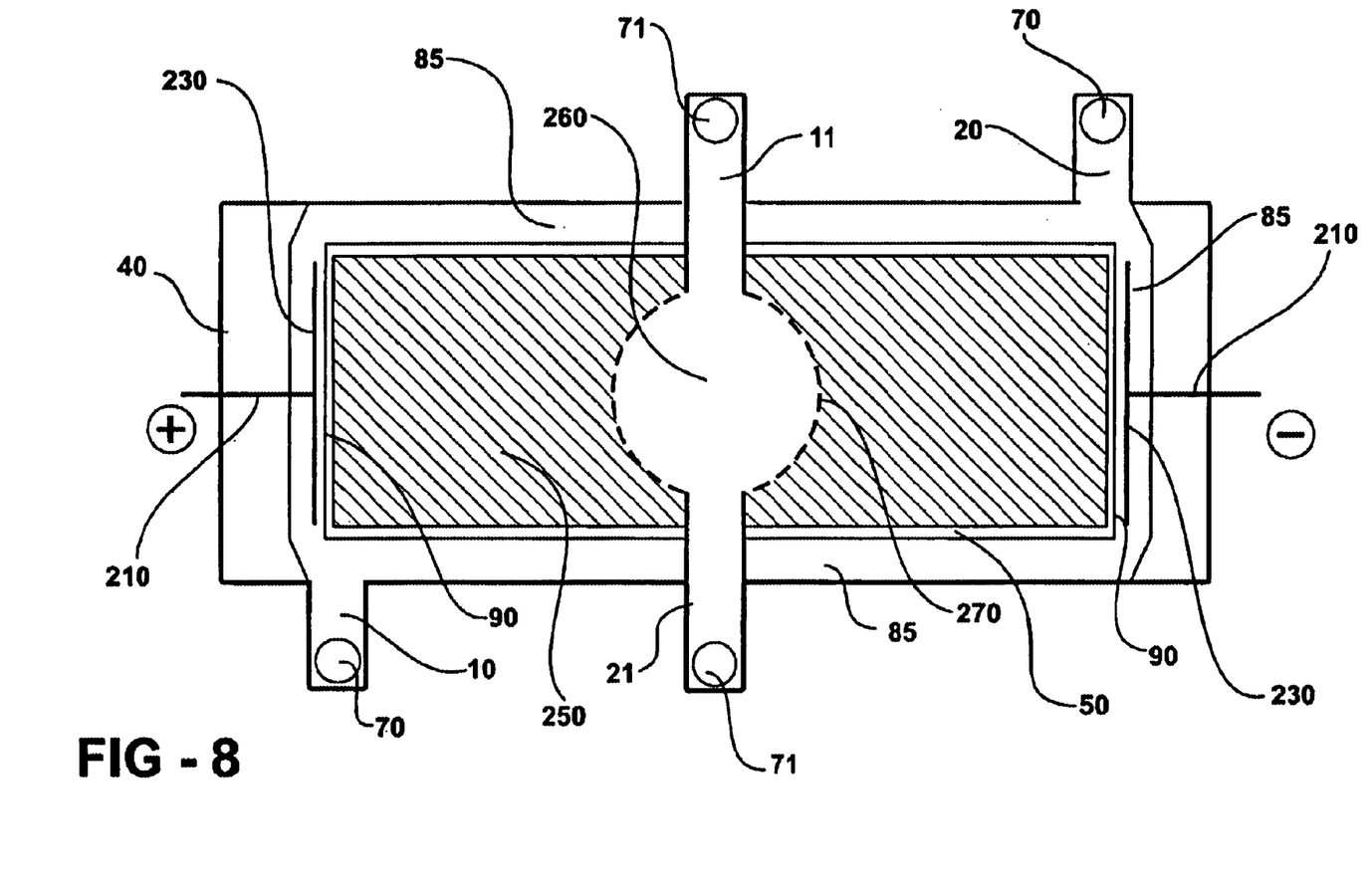
FIG. 8 is a plan view of a sixth embodiment of the invention.

In the sixth exemplary embodiment of the invention shown in FIG. 8, the reagent conduit 85 is designed to be peripheral, that is to say it is connected both to the first connection piece 10 and to the second connection piece 20. In the region of the short side walls of the preparation chamber 50, the capacitor plates 230 are arranged in the reagent conduit 85. The inner orifices 90 are located opposite the capacitor plates 230. The preparation chamber 50 receives a gel block which is separated from a preparation area 260 by a permeable barrier 270. The preparation area 260 is connected to a third connection piece 11 and a fourth connection piece 21 provided with second outer orifices 71.

Figure 9:
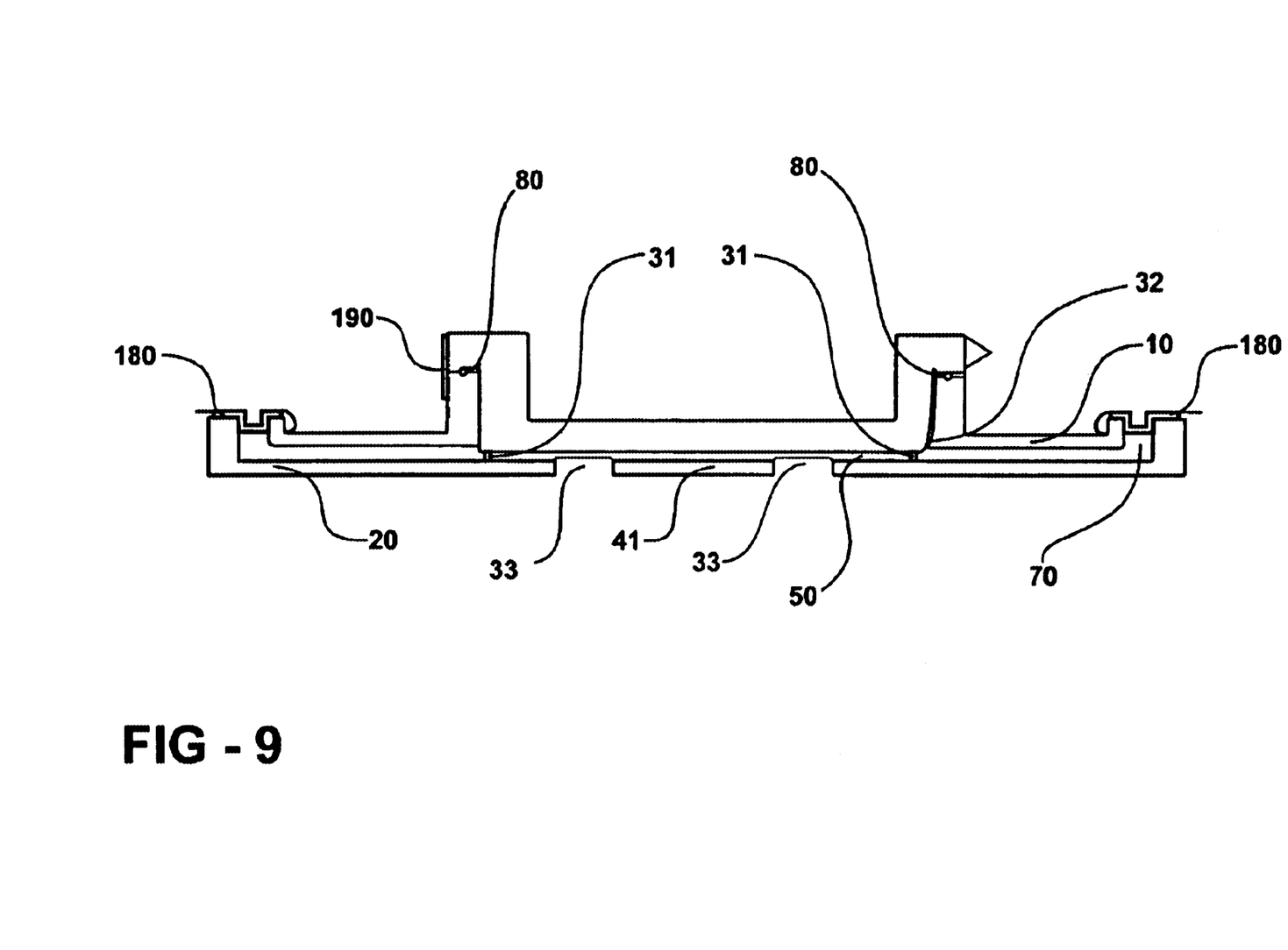
FIG. 9 is a cross section of a seventh embodiment of the invention.

In the seventh exemplary embodiment of the invention shown in FIG. 9, the bottom 41 has recesses 33 for receiving a permanent magnet. In the region of the recesses 33, the bottom is designed to be particularly thin and projects slightly into the preparation chamber 50.

What is claimed is:

1. A device for analyzing biological or medical specimens, said device comprising:

a body member having a preparation chamber, said preparation chamber defining a bottom surface;

a closure lid hingedly attached to said body member, said closure lid defining said preparation chamber formed in said body member, said closure lid and said body member defining a contact face at a region of contact therebetween when said closure lid is in a closed position;

at least a first and a second duct connected to said preparation chamber, whereby substance can be introduced into and removed from said preparation chamber when said closure lid is in said closed position, said first and second ducts each having one end opening into said preparation chamber, said one end having an inner orifice therein, said first and second ducts further having an opposite end, said opposite end having an outer orifice therein;

said closure lid further comprising a plurality of projecting spacers on the underside thereof for spacing said closure lid a predetermined distance from said bottom surface of said preparation chamber, said plurality of projecting spacers having at least one projecting spacer on which said closure lid, when in said closed position, is supported against said bottom surface of said preparation chamber; and a peripheral seal disposed at said contact face between said closure lid and said body member.

2. The device according to claim 1 wherein at least a portion of said closure lid is transparent, and further wherein said closure lid is pivotably connected to said body member.

3. The device according to claim 1, wherein at least a portion of said body member is produced from a translucent material.

4. The device according to claim 1, wherein said bottom surface of said body member is produced from a material having a thermal conductivity which is higher than the thermal conductivity of a material from which said closure lid is produced.

5. The device according to claim 4, further comprising means for heating and/or cooling said bottom surface of said preparation chamber.

6. The device according to claim 4, wherein said bottom surface further comprises at least one recess for receiving a magnet.

7. The device according to claim 1, wherein one of said body member and said closure lid has at least one electrode attached thereto.

8. The device according to claim 1, further comprising a gel block located in said preparation chamber, said gel block having a preparation area separated by a permeable barrier.

9. The device according to claim 8, wherein said second duct is located with respect to said first duct such that substance is introduced into and removed from said preparation area when said closure lid is closed.

10. The device according to claim 1, wherein said body member has at least one capacitor plate attached thereto.

11. The device according to claim 10, wherein said at least one capacitor plate comprises two capacitor plates arranged in a mutually opposing arrangement in said body member.

* * * * *